(12) United States Patent
March et al.

(10) Patent No.: US 8,445,732 B2
(45) Date of Patent: *May 21, 2013

(54) ORGANIC COMPOUNDS

(75) Inventors: Sébastien March, Meyrin (CH); Jerzy A. Bajgrowicz, Zürich (CH); Samuel Derrer, Fällanden (CH); Philip Kraft, Dübendorf (CH); Urs Mueller, Duebendorf (CH)

(73) Assignee: Givaudan SA, Vernier (CH)

( * ) Notice: Subject to any disclaimer, the term of this patent is extended or adjusted under 35 U.S.C. 154(b) by 88 days.

This patent is subject to a terminal disclaimer.

(21) Appl. No.: 12/865,403

(22) PCT Filed: Feb. 10, 2009

(86) PCT No.: PCT/CH2009/000053
§ 371 (c)(1),
(2), (4) Date: Sep. 1, 2010

(87) PCT Pub. No.: WO2009/100554
PCT Pub. Date: Aug. 20, 2009

(65) Prior Publication Data
US 2010/0331427 A1    Dec. 30, 2010

(30) Foreign Application Priority Data
Feb. 12, 2008   (GB) ................................ 0802526.4

(51) Int. Cl.
*C07C 35/06*   (2006.01)
(52) U.S. Cl.
USPC ........................................ 568/838; 424/76.2
(58) Field of Classification Search
USPC ........................................ 568/838; 424/76.2
See application file for complete search history.

(56) References Cited

U.S. PATENT DOCUMENTS

| 4,052,341 A | 10/1977 | Naipawer et al. |
| 4,610,813 A | 9/1986 | Schulte-Elte et al. |

FOREIGN PATENT DOCUMENTS

| DE | 254382 A1 | 2/1988 |
| EP | 0116903 A | 8/1984 |
| EP | 0155591 A2 | 3/1985 |
| EP | 0466019 A | 1/1992 |
| EP | 0470426 A | 2/1992 |
| EP | 0801049 A | 10/1997 |
| WO | 2006003053 A1 | 1/2006 |
| WO | 2008017183 A1 | 2/2008 |
| WO | 2008046239 A1 | 4/2008 |

OTHER PUBLICATIONS

Schoenfelder et a., Synthesis of benzene derivatives with several homochirally analogous substituentsl, Chemische Gerichte (1980), 113 (5) abstract.*
"Synthesis of Benzene Derivatives with Several Homochirally-analogous Substituents", W. Schoenfelder, et al., Sep. 6, 1979.
"Studies on the Synthetic Perfume. , II. New Aroma Chemicals Derived from (+)-2-Pinene", M. Nomura, et al., Department of Industrial Engineering, Kinki University, 1992.
Enantiospecific Synthesis, Separation and Olfactory Evaluation of all Distereomers of a Homologue of hte Sandalwood Odorant Polysantol, Castro et al., Tetrahedron, 61, 2005, 11192-11203.
XP002525758. Minor Products in Photoreactions of Alpha-Diketones with Arenes. Abstraction of Hydroxylic Hydrogen by Triplet Carbonyl, M.B. Rubin and Gutman, A. L. Journal of Organic Chemistry, vol. 51, 1986, pp. 2511-2515.
Analogues of Campholenal (=(1R)-2,2,3-Trimethylcyclopent-3-ene-1-acetaldehyde) as Building Blocks for (+)-B-Necrodol (=(1S,3S_-2,2,3-Trimethyl-4-methylenecyclopentane-methanol) and Sandalwood-like Alcohols), Christian Chapuis, et al., Verlag Helvitica Chimica Acta AG, Firmenich SA Corporate R & D Division, Geneva, 2006.
Neue Ergebnisse der Wacholderbeerol-Analyse im Hinblick auf Terperioide Inhaltsstoffe, Lamparsky, D. and L. Klimes. Parfumerie and Kosmetik, 66. Jahrgang, Nr. 9/85, Sep. 1985.

* cited by examiner

*Primary Examiner* — Jafar Parsa
(74) *Attorney, Agent, or Firm* — Norris McLaughlin & Marcus PA

(57) ABSTRACT

The present invention refers to the use as flavor or fragrance of a compound of formula (I)

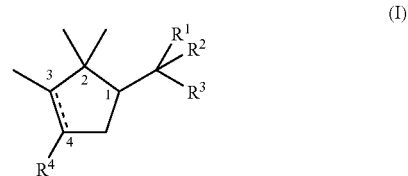

(I)

wherein
$R^4$ is hydrogen and the bond between C-3 and C-4 is a single bond or the dotted line together with the bond between C-3 and C-4 represents a double bond; or
$R^4$ is methylene, forming with C-3 and C-4 a cyclopropane ring;
$R^3$ is hydrogen, $C_1$, $C_2$, $C_3$, $C_4$, $C_5$, $C_6$ alkyl, or $C_2$, $C_3$, $C_4$, $C_5$, $C_6$ alkenyl; and
I) $R^1$ and $R^2$ together with the carbon atom to which they are attached form a carbonyl group; or
II) $R^1$ is hydroxyl and $R^2$ is selected from $C_1$, $C_2$, $C_3$ alkyl, and $C_2$, $C_3$, $C_4$ alkenyl.

7 Claims, No Drawings

ORGANIC COMPOUNDS

This is an application filed under 35 USC 371 of PCT/CH2009/000053.

The present invention refers to a novel class of campholitic aldehyde derivatives and their use as odorants. This invention furthermore relates to a method of their production and to flavour and fragrance compositions comprising them.

In the fragrance industry there is a constant demand for new compounds that enhance, modify or improve on odour notes.

Surprisingly, a new class of compounds, derived from α-campholytic aldehydes, has been found to possess valuable odour characteristics, which make them useful as fragrance ingredients. The derivatives of formula (I) as defined hereinunder have odours that range from floral (rosy), green, fruity to more agrestic, spicy and patchouli, woody.

Accordingly, the present invention refers in one of its aspects to the use as flavour or fragrance of a compound of formula (I)

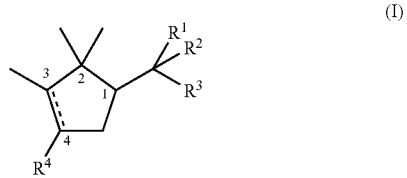

wherein
$R^4$ is hydrogen and the bond between C-3 and C-4 is a single bond or the dotted line together with the bond between C-3 and C-4 represents a double bond; or
$R^4$ is methylene, forming with C-3 and C-4 a cyclopropane ring;
$R^3$ is hydrogen, $C_1$, $C_2$, $C_3$, $C_4$, $C_5$, $C_6$ alkyl (e.g. methyl, ethyl, isobutyl), or $C_2$, $C_3$, $C_4$, $C_5$, $C_6$ alkenyl (e.g. vinyl, propenyl, 3-butenyl); and
I) $R^1$ and $R^2$ together with the carbon atom to which they are attached form a carbonyl group; or
II) $R^1$ is hydroxyl and $R^2$ is selected from $C_1$, $C_2$, $C_3$ alkyl (e.g. methyl, ethyl, n-propyl, isopropyl), and $C_2$, $C_3$, $C_4$ alkenyl (e.g. vinyl, isopropenyl, 4-pentenyl).

The compounds of formula (I) may comprise several chiral centres and as such may exist as a mixture of stereoisomers, or they may be resolved as isomerically pure forms. Resolving stereoisomers adds to the complexity of manufacture and purification of these compounds, and so it is preferred to use the compounds as mixtures of their stereoisomers simply for economic reasons. However, if it is desired to prepare individual stereoisomers, this may be achieved according to methods known in the art, e.g. preparative HPLC and GC, crystallization or by departing from chiral starting materials, e.g. starting from enantiomerically pure or enriched raw materials such as terpenoids, and/or by applying stereoselective synthesis.

Non-limiting examples are compounds of formula (I) wherein $R^4$ is hydrogen and the dotted line together with the bond between C-3 and C-4 represents a double bond.

Particular preferred is the use as flavour or fragrance of a compound of formula (I), or a is mixture thereof selected from
1-(2,2,3-trimethylcyclopent-3-enyl)propan-1-ol;
1-(2,2,3-trimethylcyclopent-3-enyl)propan-1-one;
2-(2,2,3-trimethylcyclopent-3-enyl)butan-2-ol;
2-methyl-1-(2,2,3-trimethylcyclopent-3-enyl)butan-1-ol;
3-methyl-1-(2,2,3-trimethylcyclopent-3-enyl)butan-1-ol;
1-(2,2,3-trimethylcyclopent-3-enyl)pent-4-en-1-ol;
1-(2,2,3-trimethylcyclopent-3-enyl)hex-5-en-1-ol;
2,2-dimethyl-1-(2,2,3-trimethylcyclopent-3-enyl)but-3-en-1-ol;
(E)-1-(2,2,3-trimethylcyclopent-3-enyl)but-2-en-1-ol;
(Z)-1-(2,2,3-trimethylcyclopent-3-enyl)but-2-en-1-ol;
1-(2,2,3-trimethylcyclopent-3-enyl)but-3-en-1-ol;
1-(2,2,3-trimethylcyclopent-3-enyl)ethanol;
2-methyl-1-(2,2,3-trimethylcyclopent-3-enyl)prop-2-en-1-ol;
1-(2,2,3-trimethylcyclopent-3-enyl)prop-2-en-1-ol;
2-methyl-1-(2,2,3-trimethylcyclopent-3-enyl)butan-1-one;
3-methyl-1-(2,2,3-trimethylcyclopent-3-enyl)butan-1-one;
1-(2,2,3-trimethylcyclopent-3-enyl)pent-4-en-1-one;
1-(2,2,3-trimethylcyclopent-3-enyl)hept-6-en-1-one;
2,2-dimethyl-1-(2,2,3-trimethylcyclopent-3-enyl)but-3-en-1-one;
(E)-1-(2,2,3-trimethylcyclopent-3-enyl)but-2-en-1-one;
(Z)-1-(2,2,3-trimethylcyclopent-3-enyl)but-2-en-1-one;
1-(2,2,3-trimethylcyclopent-3-enyl)but-3-en-1-one;
1-(2,2,3-trimethylcyclopent-3-enyl)ethanone;
3-(2,2,3-trimethylcyclopent-3-enyl)hex-5-en-3-ol;
2-(2,2,3-trimethylcyclopent-3-enyl)pentan-2-ol;
6-methyl-4-(2,2,3-trimethylcyclopent-3-enyl)hept-1-en-4-ol;
2-(2,2,3-trimethylcyclopent-3-enyl)hex-5-en-2-ol;
4-(2,2,3-trimethylcyclopent-3-enyl)oct-7-en-4-ol;
2-(2,2,3-trimethylcyclopent-3-enyl)oct-7-en-2-ol;
3,3-dimethyl-2-(2,2,3-trimethylcyclopent-3-enyl)pent-4-en-2-ol;
3,3-dimethyl-4-(2,2,3-trimethylcyclopent-3-enyl)hepta-1,6-dien-4-ol;
2-(2,2,3-trimethylcyclopent-3-enyl)propan-2-ol;
2,2,3-trimethylcyclopentanecarbaldehyde;
3-methyl-1-(2,2,3-trimethylcyclopentyl)butan-1-ol;
3-methyl-1-(2,2,3-trimethylcyclopentyl)butan-1-one;
6-methyl-4-(2,2,3-trimethylcyclopentyl)hept-1-en-4-ol;
2-methyl-1-(2,2,3-trimethylcyclopentyl)prop-2-en-1-ol;
(+)-(1RS,1'S,3'RS)-1-(2',2',3'-trimethylcyclopentyl);
1-(2,2,3-trimethylcyclopent-3-enyl)propan-1-ol; and
1-(1,2,2-trimethylbicyclo[3.1.0]hex-3-yl)ethanol.

The compounds according to the present invention may be used alone or in combination with known fragrances selected from the extensive range of natural and synthetic molecules currently available, such as essential oils and extracts, alcohols, aldehydes and ketones, ethers and acetals, esters and lactones, macrocycles and heterocycles.

In a further embodiment the compounds of formula (I) may be admixed with one or more ingredients or excipients conventionally used in conjunction with fragrances in fragrance applications, for example, carrier materials, and other auxiliary agents, such as solvents (e.g. dipropyleneglycol (DPG), isopropylmyristate (IPM), triethylcitrate (TEC) and alcohol (e.g. ethanol)), commonly used in the art.

The following list comprises examples of known fragrances, which may be combined with the compounds of the present invention:
  essential oils and extracts, e.g. oak moss absolute, basil oil, tropical fruit oils, such as bergamot oil and mandarin oil, mastic absolute, myrtle oil, palmarosa oil, patchouli oil, petitgrain oil, wormwood oil, lavender oil, rose oil, jasmin oil, ylang-ylang oil and sandalwood oil.
  alcohols, e.g. cis-3-hexenol, cinnamic alcohol, citronellol, Ebanol® (3-methyl-5-(2,2,3-trimethyl-3-cyclopenten-1-yl)-4-penten-2-ol), eugenol, farnesol, geraniol, menthol, nerol, rhodinol, Super Muguet™ (6-ethyl-3-methyl-6-octen-1-ol), linalool, phenylethyl alcohol, Sandalore® (5-(2,2,3-trimethyl-3-cyclopentenyl)-3-methylpentan-2-ol), terpineol or Timberol® (1-(2,2,6-trimethylcyclohexyl)hexan-3-ol).

aldehydes and ketones, e.g. citral, hydroxycitronellal, Lilial® (3-(4-tert-butylphenyl)-2-methylpropanal), methylnonylacetaldehyde, anisaldehyde, allylionone, verbenone, nootkatone, geranylacetone, α-amylcinnamic aldehyde, Georgywood™ (1-(1,2,8,8-tetramethyl-1,2,3,4,5,6,7,8-octahydronaphthalen-2-yl)ethanone), hydroxycitronellal, Iso E Super® (1-(2,3,8,8-tetramethyl-1,2,3,4,5,6,7,8-octahydronaphthalen-2-yl)ethanone), Isoraldeine® (4-(2,6,6-trimethyl-2-cyclohexenyl)-3-methyl-3-buten-2-one), Hedione® (methyl (3-oxo-2-pentylcyclopentyl)acetate), maltol, methyl cedryl ketone, and vanillin.

ethers and acetals, e.g. Ambrox® (3a,6,6,9a-tetramethyl-dodecahydronaphtho[2,1-b]furan), geranyl methyl ether, rose oxide or Spirambrene (2,2,3',7',7'-pentamethylspiro(1,3-dioxan-5,2'-norcarane)).

esters and lactones, e.g. benzyl acetate, cedryl acetate, γ-decalactone, Helvetolide® (2-[1-(3,3-dimethylcyclohexyl)ethoxy]-2-methylpropan-1-ol propanoate), γ-undecalactone, vetivenyl acetate, cinnamyl propionate, citronellyl acetate, decyl acetate, dimethylbenzylcarbinyl acetate, ethyl acetoacetate, ethyl acetylacetate, cis-3-hexenyl isobutyrate, linalyl acetate and geranyl acetate.

macrocycles, e.g. Ambrettolide, Ethylene brassylate or Exaltolide® (oxacyclohexadecan-2-one).

heterocycles, e.g. isobutylchinoline.

The compounds of the present invention may be used in a broad range of fragranced applications, e.g. in any field of fine and functional perfumery, such as perfumes, household products, laundry products, body care products and cosmetics.

The compounds of formula (I) can be employed in widely varying amounts, depending upon the specific application and on the nature of the composition or application one intends to fragrance, for example the nature and quantity of co-ingredients, and the particular effect that the perfumer seeks. In general, the proportion is typically from 0.001 to 20 weight percent of the application. In one embodiment, compounds of the present invention may be employed in a fabric softener in an amount of from 0.001 to 0.05 weight percent. In another embodiment, compounds of the present invention may be used in an alcoholic solution in amounts of from 0.1 to 30 weight percent, more preferably between 1 and 20 weight percent. However, these values are given only by way of example, since the experienced perfumer may also achieve effects or may create novel accords with lower or higher concentrations, e.g. up to about 50 weight percent based on the composition.

The compounds of the present invention may be employed into a consumer product base by mixing a compound of formula (I), a mixture thereof or fragrance composition comprising it, with the consumer product base, and/or they may, in an earlier step, be entrapped with an entrapment material such as polymers, capsules, microcapsules and nanocapsules, liposomes, film formers, absorbents such as carbon or zeolites, cyclic oligosaccharides and mixtures thereof, and/or they may be chemically bonded to substrates, which together with the substrate forms a precursor, which are adapted to release the compound of formula (I) upon application of an external stimulus such as light, enzyme, or the like, and then mixed with the consumer product base.

The invention additionally provides a method of manufacturing a fragrance application comprising the incorporation of a compound of formula (I) as fragrance ingredient, either by admixing the compound to the consumer product base or by admixing a composition comprising a compound of formula (I) or a precursor thereof, which may then be mixed to the consumer product base, using conventional techniques and methods. Through the addition of an organoleptically acceptable amount of a compound of formula (I) or a mixture thereof, the organoleptic properties of the consumer product base will be improved, enhanced or modified.

By "precursors" is meant, in particular, reaction products of the aldehydes/ketones of formula (I), i.e. compounds of formula (I) wherein $R^1$ and $R^2$ together with the carbon atom to which they are attached form a carbonyl group, with a compound comprising at least one functional group selected from the group of primary amine, secondary amine, sulfhydryl (thiol), hydroxyl and carboxyl, in which a covalent bond is formed between at least one carbon atom of the compound of formula (I) and at least one of the hetero atoms of said compounds comprising at least one functional group selected from the group of N, S and O.

The invention furthermore provides a method for improving, enhancing or modifying a consumer product base by means of the addition thereto of an olfactorily acceptable amount of a compound of formula (I), or a mixture thereof.

The invention also provides a fragrance application comprising:
a) as fragrance a compound of formula (I) or a mixture thereof; and
b) a consumer product base.

As used herein, by "consumer product base" is meant a formulation for use as a consumer product to fulfill specific actions, such as cleaning, softening, and caring or the like. Examples of such products include fine perfumery, e.g. perfume and eau de toilette; fabric care, household products and personal care products such as laundry care detergents, rinse conditioner, personal cleansing products, detergent for dishwasher, surface cleaner; laundry products, e.g. softener, bleach, detergent; body care products, e.g. shampoo, shower gel; air care products and cosmetics, e.g. deodorant, and vanishing crème. This list of products is given by way of illustration and is not to be regarded as being in any way limiting.

Most of the compounds of formula (I) are described hereinabove for the first time and thus are novel in their own right. To the best of our knowledge, among the compounds of formula (I) only a few are known. 2,2,3-Trimethylcyclopent-3-enecarbaldehyde was found in traces in juniperberry oil (Lamparsky et al., Parfuemerie and Kosmetik (1985), 66(9), 553-6, 558-60). 2,2,3-Trimethylcyclopentanecarbaldehyde is mentioned as an intermediate by M. B. Rubin and A. L. Gutman in Journal of Organic Chemistry (1986), 51(13), 2511-5. 1-(2,2,3-Trimethylcyclopent-3-enyl)ethanol is mentioned as an intermediate in WO 2008/046239. However, no odour properties are disclosed.

Thus, the present invention refers in a further aspect to compounds of formula (I)

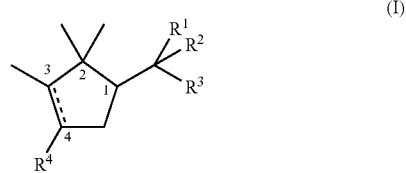

wherein
- R$^4$ is hydrogen and the bond between C-3 and C-4 is a single bond or the dotted line together with the bond between C-3 and C-4 represents a double bond; or
- R$^4$ is methylene, forming with C-3 and C-4 a cyclopropane ring;
- R$^3$ is hydrogen, C$_1$, C$_2$, C$_3$, C$_4$, C$_5$, C$_6$ alkyl (e.g. methyl, ethyl, isobutyl), or C$_2$, C$_3$, C$_4$, C$_5$, C$_6$ alkenyl (e.g. vinyl, propenyl, 3-butenyl); and
- I) R$^1$ and R$^2$ together with the carbon atom to which they are attached form a carbonyl group; or
- II) R$^1$ is hydroxyl and R$^2$ is selected from C$_1$, C$_2$, C$_3$ alkyl (methyl, ethyl, n-propyl, isopropyl), and C$_2$, C$_3$, C$_4$ alkenyl (e.g. vinyl, isopropenyl, 4-pentenyl);

with the proviso that 2,2,3-trimethyl-cyclopent-3-enecarbaldehyde, 2,2,3-trimethylcyclopentanecarbaldehyde, and 1-(2,2,3-trimethylcyclopent-3-enyl)ethanol are excluded.

The compounds of formula (I) may be prepared starting from the commercially-available α-campholenic aldehyde of any enantiomeric ratio (pure (R) or (S) or any mixture of both enantiomers, e.g. from about 9:1 to about 1:9 (R/S)) via the corresponding quality of its lower homologue, α-campholytic aldehyde, described in the literature by Ch. Chapuis et al., Helvetica Chimica Acta 2006, 89, 2638-2653. The latter may be converted by reaction with Grignard reagents to the corresponding secondary alcohols, which in turn can be oxidised with pyridinium chlorochromate to the corresponding ketones. These again can be subjected to a Grignard reaction to obtain the tertiary alcohols described herein. Alternatively, α-campholytic aldehyde can be hydrogenated, e.g. under palladium on-carbon catalysis, to obtain the corresponding saturated derivative, 2,2,3-trimethyl-cyclopentanecarbaldehyde, which can be submitted to the reaction described above in order to produce the corresponding saturated secondary or tertiary alcohols or the ketones. Yet another possibility is to cyclopropanate α-campholytic aldehyde or an alcohol derived therefrom (see above) and submit the product to the transformation described previously (i.e. Grignard reagent addition and oxidation of alcohols to the corresponding ketones) under conditions known to the person skilled in the art.

Campholytic alcohol is obtainable from α-campholenic aldehyde, e.g. via sodium borohydride reduction.

Further particulars as to reaction conditions are provided in the examples.

The invention is now further described with reference to the following non-limiting examples. These examples are for the purpose of illustration only and it is understood that variations and modifications can be made by one skilled in the art.

All products described in the Examples were obtained starting from commercially-available qualities of α-campholenic aldehyde of approximately 9:1 or 2:3 (R/S) enantiomer ratios. Flash chromatography: Merck silica gel 60 (230-400 mesh). The reported NMR spectra were measured in CDCl$_3$; chemical shifts (δ) are reported in ppm downfield from TMS; coupling constants J in Hz.

EXAMPLE 1

1-(2,2,3-trimethylcyclopent-3-enyl)propan-1-ol

A solution of α-campholytic aldehyde (10 g, 72 mmol, 20.6% ee (R)) in 11 mL THF is added drop-wise into a cooled, mechanically stirred solution of ethylmagnesium bromide (40 mL, 87 mmol, 2.2 M in THF) at a rate allowing the mixture temperature to be kept between −10° C. and 0° C. (ca. 20 min). The resulting solution is stirred for 2 h while the temperature is allowed to warm to 0° C. The resulting heterogeneous mixture is quenched with 100 mL of 2M HCl. The aqueous layer is extracted with MTBE and the combined organic layers are dried over MgSO$_4$, then evaporated yielding 11.9 g of a yellow liquid (98% yield). This material can be purified by distillation or chromatography, but was used directly in the next step.

Odour description: very natural, agrestic, patchouli, a bit earthy/mossy, fruity (fenchyl acetate-type), slightly green.

$^1$H NMR (400 MHz, CDCl$_3$) δ5.26 (broad s, 1H); 3.66 (dt, 8.1, 4.6 Hz, 1H); 2.24 (m, 2H); 1.87 (td, 8.2, 4.8 Hz, 1H); 1.58 (m, 3H); 1.6-1.4 (m, 2H); 1.42 (broad s, 1H); 1.01 (s, 3H); 0.96 (t, 7.3 Hz, 3H); 0.95 (s, 3H).

$^{13}$C NMR (100 MHz, CDCl$_3$) δ148.2 (C$^{IV}$); 121.8 (CH); 73.4 (CH); 54.3 (CH); 46.7 (C$^{IV}$); 30.4 (CH$_2$); 29.6 (CH$_2$); 27.0 (CH$_3$); 20.5 (CH$_3$); 12.4 (CH$_3$); 10.3 (CH$_3$).

MS (EI, m/z) 168 (2, M$^+$); 150 (16); 135 (18); 121 (100); 107 (18); 95 (88); 79 (14); 67 (20); 59 (16); 55 (16); 41 (23).

EXAMPLE 2

1-(2,2,3-trimethylcyclopent-3-enyl)propan-1-one

A solution of the product obtained in example 1 (7.3 g, 43 mmol) in 40 mL DCM is added drop-wise within 20 min into a magnetically stirred suspension of pyridinium chlorochromate (10.3 g, 48 mmol) and Celite (10.4 g) in 130 mL DCM at rt. The resulting brown mixture is stirred at rt for 18 h and filtered through a silica plug. The solvents are evaporated yielding 6.77 g of a yellow liquid (94% yield). This material can be purified by distillation or chromatography, but was used directly in the next step.

Odour description: herbaceous, slightly minty; +4 h: green, citrus, herbaceous, floral $^1$H NMR (400 MHz, CDCl$_3$) δ5.21 (m, 1H); 2.94 (t, 8.5 Hz, 1H); 2.7-2.6 (m, 1H); 2.5-2.3 (m, 2H); 2.2-2.1 (m, 1H); 1.57 (m, 3H); 1.22 (s, 3H); 1.03 (t, 7.2 Hz, 3H); 0.78 (s, 3H).

$^{13}$C NMR (100 MHz, CDCl$_3$) δ212.4 (C$^{IV}$); 145.6 (C$^{IV}$); 121.3 (CH); 61.7 (CH); 48.7 (C$^{IV}$); 37.2 (CH$_2$); 31.5 (CH$_2$); 27.6 (CH$_3$); 21.3 (CH$_3$); 12.1 (CH$_3$); 7.6 (CH$_3$).

MS (EI, m/z) 166 (36, M$^+$); 151 (11); 137 (25); 123 (35); 109 (45); 93 (17); 79 (17); 67 (35); 57 (100); 41 (22).

EXAMPLE 3

2-(2,2,3-trimethylcyclopent-3-enyl)butan-2-ol

A solution of the product obtained in example 2 (2.3 g, 14 mmol) in 2 mL THF is added drop-wise into a cooled, magnetically stirred solution of methylmagnesium chloride (6.4 mL, 18 mmol, 22% in THF) at a rate allowing the mixture temperature to be kept between −10° C. and 0° C. (ca. 30 min). The resulting solution is stirred for 3.3 h while the temperature is allowed to warm to 0° C. The resulting heterogeneous mixture is quenched with 2M HCl and diluted with MTBE. The aqueous layer is extracted once with MTBE. The combined organic layers are dried over MgSO$_4$ and evaporated yielding 2.4 g of a brown liquid (quantitative yield). This material was purified by chromatography.

Odour description: earthy, slightly woody, fruity, agrestic, camphoraceous; +4 h: earthy, humus, green; +24 h: earthy, green, watery, mossy $^1$H NMR (400 MHz, CDCl$_3$ δ5.24 (m, 1H); 2.3-2.2 (m, 1H); 2.2-2.1 (m, 1H); 2.01 (dd, 10.6 8.1 Hz, 1H); 1.64 (q, 7.6 Hz, 2H); 1.55 (m, 3H); 1.17 (s, 3H); 1.15 (s, 3H); 1.07 (s, 3H); 0.93 (t, 7.5 Hz, 3H).

$^{13}$C NMR (100 MHz, CDCl$_3$) δ148.3 (C$^{IV}$); 121.0 (CH); 75.4 (C$^{IV}$); 57.4 (CH); 47.8 (C$^{IV}$); 34.7 (CH$_2$); 31.6 (CH$_2$); 28.5 (CH$_3$); 26.0 (CH$_3$); 21.5 (CH$_3$); 12.3 (CH$_3$); 8.2 (CH$_3$).

MS (EI, m/z) 167 (1); 164 (8); 153 (5); 149 (3); 135 (28); 109 (10); 95 (68); 73 (100); 55 (33); 43 (64).

EXAMPLE 4

Following the general procedure according to Example 1 the compounds 4.1 to 4.12 (see Table 1) were prepared from α-campholytic aldehyde of approximately 9:1 or 2:3 (R/S) enantiomeric ratios.

EXAMPLE 5

Following the general procedure according to Example 2, the compounds 5.1 to 5.13 (see Table 1) were prepared from the appropriate secondary alcohol obtained as in Example 4.

EXAMPLE 6

Following the general procedure according to Example 3, the compounds 6.1 to 6.9 (see Table 1) were prepared from the appropriate ketone obtained as in Example 5.

TABLE 1

| | | | Odour description |
|---|---|---|---|
| 4.1 | 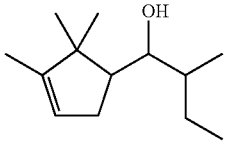 | MS (EI, m/z) 196 (1, M$^+$); 178 (9); 163 (7); 149 (8); 121 (100); 108 (41); 95 (60); 55 (20); 41 (32). | floral, green; +4 h: floral, green, rosy, slightly metallic; +24 h: weak, floral, green, fruity. |
| 4.2 | 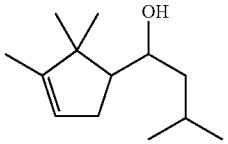 | MS (EI, m/z) 196 (1, M$^+$); 178 (9); 163 (6); 135 (10); 121 (66); 107 (38); 95 (100); 79 (19); 67 (20); 55 (19); 41 (34). | metallic on top then floral, green, fruity, spicy, +4 h: floral, green, slightly fruity, rosy, soft; +24 h: weak, green, floral, slightly fruity, rosy. |
| 4.3 | 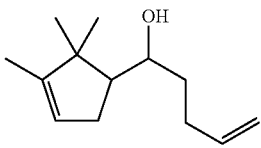 | MS (EI, m/z) 194 (2, M$^+$); 176 (3); 161 (16); 139 (3); 135 (18); 121 (37); 109 (27); 95 (100); 67 (29); 55 (32); 41 (37). | slightly aromatic, fruity, floral; +4 h: fruity, slightly green, balsamic; +24 h: weak, slightly floral, fresh, green. |
| 4.4 | 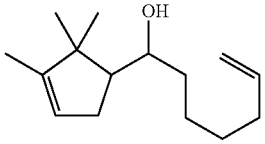 [SMILES: C=CCCCCC(O)C1CC=C(C)C1(C)C] | MS (EI, m/z) 222 (1, M$^+$); 204 (7); 189 (4); 175 (3); 161 (5); 147 (8); 135 (8); 121 (73); 108 (26); 95 (100); 79 (19); 67 (25); 55 (34); 41 (39). | floral, green, weak, +24 weak, floral |
| 4.5 | 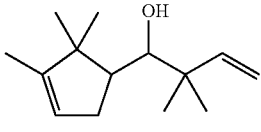 | MS (EI, m/z) 208 (2, M$^+$); 190 (2); 175 (4); 138 (45); 123 (52); 121 (89); 109 (55); 95 (90); 79 (28); 70 (100); 55 (73); 43 (81); 41 (83). | floral, green, powdery, slightly rosy; +4 h: weak, agrestic, slightly minty, woody; +24 h: weak, almost odorless |
| 4.6* | 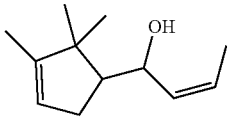 | MS: m/z (%) = 27 (5) [C$_2$H$_3$$^+$], 41 (26) [C$_3$H$_5$], 55 (20) [C$_4$H$_7$$^+$], 71 (45) [C$_4$H$_5$OH$^+$], 79 (19), 95 (16) [C$_7$H$_{11}$$^+$], 109 (44) [C$_8$H$_{13}$$^+$], 121 (8) [C$_9$H$_{13}$$^+$], 147 (21) [M$^+$ − H$_2$O − CH$_3$], 162 (12) [M$^+$ − H$_2$O], 180 (2) [M$^+$]. | powdery, reminiscent of Cacao beans, agrestic, green, floral; +4 h: weak, agrestic; +24 h: green, floral, a bit sandalwood. |
| 4.7* | 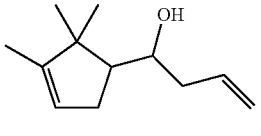 | MS: m/z (%) = 27 (5) [C$_2$H$_3$$^+$], 41 (31) [C$_3$H$_5$], 55 (23) [C$_4$H$_7$$^+$], 67 (24) 79 (20), 95 (77) [C$_7$H$_{11}$$^+$], 105 (19), 121 (100) [M$^+$ − C$_3$H$_5$ − H$_2$O], 139 (19) [M$^+$ − C$_3$H$_5$], 147 (13) [M$^+$ − H$_2$O − CH$_3$], 162 (6) [M$^+$ − H$_2$O], 180 (1) [M$^+$]. | green, agrestic, fruity, +4 h: weak floral, agrestic; +24 h: green, floral, fruity |
| 4.8** | 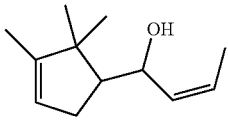 | MS: m/z (%) = 27 (5) [C$_2$H$_3$$^+$], 41 (26) [C$_3$H$_5$], 55 (20) [C$_4$H$_7$$^+$], 71 (45) [C$_4$H$_6$OH$^+$], 79 (19), 95 (16) [C$_7$H$_{11}$$^+$], 109 (44) [C$_5$H$_{13}$$^+$], 121 (8) [C$_9$H$_{13}$$^+$], 147 (21) [M$^+$ − H$_2$O − CH$_3$], 162 (12) [M$^+$ − H$_2$O], 180 (2) [M$^+$]. | green, agrestic, floral; +4 h: agrestic, +24 h: weak cream |
| 4.9* | 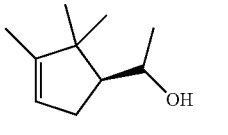 | MS: m/z (%) = 41 (9) [C$_3$H$_5$$^+$], 45 (12) [C$_2$H$_4$OH$^+$], 55 (8) [C$_4$H$_7$$^+$], 67 (17) [C$_5$H$_7$$^+$], 79 (9) [C$_5$H$_7$$^+$], 91 (6) [C$_7$H$_7$$^+$], 95 (100) [C$_7$H$_{11}$$^+$], 105 (3) [C$_8$H$_9$$^+$], 109 (4) [C$_5$H$_{13}$$^+$], 121 (37) [M$^+$ − CH$_3$ − H$_2$O], 136 (13) [M$^+$ − H$_2$O], 139 (1) [M$^+$ − CH$_3$], 154 (4) [M$^+$]. Polarimetry (c 0.96 in EtOH): [α]$_D$$^{22}$ = +6.8°, [α]$_{578}$$^{22}$ = +7.1°, [α]$_{546}$$^{22}$ = +8.2°, [α]$_{436}$$^{22}$ = +14.7°, [α]$_{365}$$^{22}$ = +23.3°. | typical clean patchouli scent woody-camphoraceous-earthy, with slightly spicy accents and fruity-green facets, and some reminiscence to borneol. |

TABLE 1-continued

| | | | Odour description |
|---|---|---|---|
| 4.10** | (structure: cyclopentene with CH(OH)CH₃ substituent) | MS: m/z (%) = 41 (11) [$C_2H_5^+$], 45 (16) [$C_2H_4OH^+$], 55 (10) [$C_4H_7^+$], 67 (18) [$C_5H_7^+$], 79 (9) [$C_6H_7^+$], 91 (6) [$C_7H_7^+$], 95 (100) [$C_7H_{11}^+$], 105 (3) [$C_8H_9^+$], 109 (4) [$C_8H_{13}^+$], 121 (35) [$M^+ - CH_3 - H_2O$], 136 (12) [$M^+ - H_2O$], 139 (1) [$M^+ - CH_3$], 154 (3) [$M^+$]. Polarimetry (c 0.37 in EtOH): $[\alpha]_D^{22} = -26.3°$, $[\alpha]_{578}^{22} = -27.1°$, $[\alpha]_{546}^{22} = -31.1°$, $[\alpha]_{436}^{22} = -55.8°$, $[\alpha]_{365}^{22} = -94.2°$. | borneol- and patchouli-like note, with woody-earthy aspects |
| 4.11* | (structure) | MS: m/z (%) = 27 (6) [$C_2H_3^+$], 41 (40) [$C_3H_5^+$], 55 (27) [$C_4H_7^+$], 67 (52), 71 (28), 79 (22), 95 (100) [$C_7H_{11}^+$], 108 (69), 123 (6), 139 (8) [$M^+ - C_3H_5$], 47 (8) [$M^+ - CH_3 - H_2O$], 165 (31) [$M^+ - CH_3$], 180 (2) [$M^+$]. | Fruity (pear), agrestic; +4 h: agrestic, minty, fruity; +24 h: very weak fruity. |
| 4.12 | (structure) | MS (EI, m/z) 166 (4, $M^+$); 151 (9); 148 (6); 133 (23); 109 (39); 95 (100); 67 (42); 57 (27); 41 (19). Polarimetry (c 1.06 in EtOH): $[\alpha]_D^{22} = +0.4°$, $[\alpha]_{578}^{22} = +0.5°$, $[\alpha]_{546}^{22} = +0.6°$, $[\alpha]_{436}^{22} = +1.3°$, $[\alpha]_{365}^{22} = +2.3°$ | patchouli, spicy, anisic, badiane, linear; dry down: camphoraceous, woody, patchouli, anisic, black licorice, cinnamic, earthy, honey. |
| 5.1 | (structure) | MS (EI, m/z) 194 (30, $M^+$); 179 (5); 151 (17); 137 (61); 109 (100); 85 (24); 67 (41); 57 (99); 41 (37). | floral, freesia, green, glycolierral fruity; +4 h: floral, green, fruity, linalool-like; +24 weak floral. |
| 5.2 | (structure) | MS (EI, m/z) 194 (36, $M^+$); 179 (13); 151 (30); 137 (36); 109 (55); 85 (61); 79 (19); 67 (31); 57 (100); 41 (43). | floral, green, rosy; +4 h: floral, green, rosy, fruity; +24 h: weak floral. |
| 5.3 | (structure) | MS (EI, m/z) 192 (29, $M^+$); 177 (13); 149 (11); 137 (17); 109 (41); 93 (16); 83 (21); 79 (18); 67 (29); 55 (100); 41 (28). | sweet, agrestic, green, fruity; +4 h: green, agrestic; +24 h: weak green. |
| 5.4 | (structure) | MS (EI, m/z) 220 (37, $M^+$); 205 (11); 177 (6); 137 (38); 109 (54); 93 (25); 83 (29); 67 (40); 55 (100); 41 (53). | green, fatty, slightly metallic; +4 h: green, lactonic, powdery; +24 h: weak, slightly green, powder, woody. |
| 5.5 | (structure) | MS (EI, m/z) 206 (4, $M^+$); 137 (19); 109 (100); 91 (6); 81 (14); 67 (37); 55 (13); 41 (29). | aromatic, floral, woody, slightly spicy; +4 h: floral, aromatic slightly calamus, woody; +24 h: weak aromatic. |
| 5.6* | (structure) | MS: m/z (%) = 27 (2) [$C_2H_3^+$], 41 (30) [$C_3H_5^+$], 55 (10) [$C_4H_7^+$], 69 (100) [$C_4H_5O^+$], 79 (15), 93 (13), 109 (21) [$C_6H_{13}^+$], 121 (6) [$C_9H_{13}^+$], 135 (23) [$M^+ - C_3H_7$], 163 (24) [$M^+ - CH_3$], 178 (31) [$M^+$] | Green metallic, fruity, agrestic; +4 h: weak, fruity, agrestic; +24 h: weak fruity. |
| 5.7** | (structure) | MS: m/z (%) = 27 (3) [$C_2H_3^+$], 41 (35) [$C_3H_5^+$], 51 (3), 55 (15), 67 (46), 69 (26) [$C_4H_5O^+$], 77 (14), 81 (17), 91 (12), 109 (100) [$C_8H_{13}^+$], 137 (35) [$C_9H_{13}O^+$], 163 (5) [$M^+ - CH_3$], 178 (16) [$M^+$] | fruity, slightly tobacco-balsamic and powdery, natural, a bit rhubarb |
| 5.8* | (structure) | MS: m/z (%) = 27 (3) [$C_2H_3^+$], 41 (35) [$C_3H_5^+$], 51 (3), 55 (15), 67 (46), 69 (26) [$C_4H_5O^+$], 77 (14), 81 (17), 91 (12), 109 (100) [$C_8H_{13}^+$], 137 (35) [$C_9H_{13}O^+$], 163 (5) [$M^+ - CH_3$], 178 (16) [$M^+$] | fruity, mouthwatering, food-like; +4 h: still fruity, plum-fig; +24 h: weak fruity. |

TABLE 1-continued

| | | | Odour description |
|---|---|---|---|
| 5.9** | (structure) | MS: m/z (%) = 27 (2) [$C_2H_3^+$], 41 (30) [$C_3H_5^+$], 55 (10) [$C_4H_7^+$], 69 (100) [$C_4H_5O^+$], 79 (15), 93 (13), 109 (21) [$C_6H_{13}^+$], 121 (6) [$C_9H_{13}^+$], 135 (23) [$M^+ - C_3H_7$], 163 (24) [$M^+ - CH_3$], 178 (31) [$M^+$] | fruity, slightly green-matallic; +4 h: fruity-green, slightly pineapple; +24 h: floral-green, weak. |
| 5.10* | (structure) | MS: m/z (%) = 43 (100) [$C_2H_3O^+$], 67 (31) [$C_5H_7^+$], 79 (16) [$C_6H_7^+$], 91 (14) [$C_7H_7^+$], 94 (7) [$M^+ - C_3H_5O^+$], 95 (38) [$C_7H_{11}^+$], 109 (67) [$M^+ - CH_3 - CO$], 119 (2) [$M^+ - CH_3 - H_2O$], 137 (21) [$M^+ - CH_3$], 152 (38) [$M^+$].<br>Polarimetry (c 1.02 in EtOH): $[\alpha]_D^{22} = +8.7°$, $[\alpha]_{578}^{22} = +9.1°$, $[\alpha]_{546}^{22} = +10.2°$, $[\alpha]_{436}^{22} = +14.8°$, $[\alpha]_{365}^{22} = +8.4°$. | herbaceous, sweet, floral jasmine note, with ethereal, fruity, green-aromatic and somewhat patchouli-type facets. |
| 6.1 | (structure) | MS (EI, m/z) 179 (2); 167 (5); 149 (6); 109 (7); 95 (12); 69 (10); 57 (100); 41 (17). | fruity, agrestic, slightly metallic; +4 h: fruity, agrestic, slightly woody; +24 h: floral, green, fruity. |
| 6.2 | (structure) | MS (EI, m/z) 192 (9); 177 (3); 153 (14); 135 (24); 121 (14); 109 (22); 101 (55); 95 (72); 79 (16); 67 (15); 57 (65); 43 (100). | weak, floral; +4 h: weak, herbaceous, green; +24 h: weak, slightly herbaceous. |
| 6.3 | (structure) | MS (EI, m/z) 218 (1); 195 (4); 179 (5); 177 (5); 137 (3); 121 (7); 109 (11); 95 (16); 85 (100); 69 (17); 57 (85); 41 (35). | green, herbaceous, slightly fruity; +4 h: fruity, metallic, slightly green, floral; +24 h: weak, green, slightly fruity. |
| 6.4 | (structure) | MS (EI, m/z) 190 (2); 175 (3); 153 (5); 135 (7); 109 (8); 99 (12); 95 (33); 79 (8); 67 (7); 55 (14); 43 (100). | earthy, spicy, sweet, green; +4 h: earthy, spicy, caryophylenic, green; +24 h: earthy, floral, watery, green. |
| 6.5 | (structure) | MS (EI, m/z) 218 (3); 203 (1); 193 (4); 181 (4); 175 (5); 16 (4); 127 (20); 109 (7); 95 (24); 83 (24); 71 (100); 55 (33); 43 (37). | slightly agrestic, woody, weak; +4 h: weak woody; +24 h: weak, slightly woody. |
| 6.6 | (structure) | MS (EI, m/z) 218 (6); 203 (3); 175 (2); 61 (1); 153 (11); 135 (29); 127 (4); 109 (29); 95 (47); 79 (11); 67 (14); 55 (24); 43 (100). | weak, green, earthy; +4 h: weak; green; +24 h: very weak, green |
| 6.7 | (structure) | MS (EI, m/z) 153 (26); 113 (3); 109 (25); 95 (9); 69 (9); 55 (9); 43 (100). | slightly floral, green, rice floralcy; +4 h: weak, green, slightly floral; +24 h: weak, floral, green, fresh. |
| 6.8 | (structure) | MS (EI, m/z) 207 (1); 179 (12); 161 (1); 137 (11); 121 (1); 109 (28); 95 (6); 79 (6); 69 (100); 55 (14); 41 (42). | Green, fatty, fruity; +4 h: weak: green, fruity +24 h: very weak green. |

TABLE 1-continued

| | | | Odour description |
|---|---|---|---|
| 6.9* | 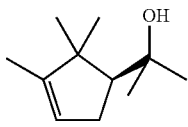 | MS: m/z (%) = 43 (31) [$C_2H_2O^+$], 59 (100) [$C_3H_6OH^+$], 67 (13) [$C_5H_7^+$], 79 (10) [$C_6H_7^+$], 91 (9) [$C_7H_7^+$], 95 (83) [$C_7H_{11}^+$], 119 (3) [$C_9H_{11}^+$], 135 (51) [$M^+ - H_2O - CH_3$], 150 (16) [$M^+ - H_2O$], 153 (3) [$M^+ - CH_3$], 168 (1) [$M^+$]. Polarimetry (c 0.96 in EtOH): $[\alpha]_D^{22} = +10.1°$, $[\alpha]_{578}^{22} = +10.5°$, $[\alpha]_{546}^{22} = +21.1°$, $[\alpha]_{436}^{22} = +21.6°$, $[\alpha]_{365}^{22} = +35.9°$. | borneol-type, woody-earthy note reminding patchouli oil with additional agrestic, fresh aromatic and slightly musky accents. |

*1S, ca. 20% ee
**1R, ca. 80% ee

EXAMPLE 7

2,2,3-trimethylcyclopentanecarbaldehyde

To a solution of α-campholytic aldehyde (5 g, 36 mmol, 20.6% ee (R)) in n-butanol/ethyl acetate (1:1, 36 mL), is added palladium on charcoal (5%, 0.3 g). The mixture is magnetically stirred for 18 h under an atmosphere of hydrogen (balloon fitted), after which GC-monitoring showed the reaction to be virtually completed. The mixture is filtered through a plug of celite and the filtrate reduced in vacuo to afford the required 2,2,3-trimethylcyclopentanecarbaldehyde as colourless odoriferous liquid (5.1 g, quantitative yield, purity >95%). This material was used directly in the next step.

$^1$H NMR (400 MHz, CDCl$_3$) δ9.75 (1H, d, 3.5, CHO), 2.39 (dt, 3.5, 9.5, C$^1$H), 2.08-1.97 (1H, m, CH), 1.92-1.83 (1H, m, CH), 1.76-1.60 (2H, m, 2×CH), 1.41-1.29 (1H, m, CH), 1.16 (3H, s, CH$_3$), 0.85 (3H, d, 6.5, Me-C$^3$), 0.72 (3H, s, CH$_3$).

$^{13}$C NMR (100 MHz, CDCl$_3$) δ205.4 (CHO); 62.4 (CH); 46.0 (CH); 44.8 (C$^{IV}$); 30.6 (CH$_2$); 26.6 (CH$_3$); 21.2 (CH$_2$); 15.8 (CH$_3$); 12.7 (CH$_3$).

MS (EI, m/z) 140 (8, M$^+$); 125 (16); 107 (20); 97 (49); 83 (82); 69 (100); 55 (79); 41 (73).

Odour description: agrestic, camphoraceous, balsamic, fruity, pine.

EXAMPLE 8

Further Compounds

Following the general procedure according to Example 1, Example 2 or Example 3 the following compound was prepared from 2,2,3-trimethylcyclopentancarbaldehyde (dihydro-campholyte aldehyde).

8.1: 3-methyl-1-(2,2,3-trimethylcyclopentyl)butan-1-ol

Odour description: agrestic, green

MS (EI, m/z) 180 (1); 165 (2); 141 (14); 123 (100); 112 (34); 95 (22); 81 (22); 69 (90); 57 (44); 41 (47).

8.2: 3-methyl-1-(2,2,3-trimethylcyclopentyl)butan-1-one

Odour description: fruity apple, sparkling, interesting; +4 h: fruity, like agrumex, herbaceous; +24 h: weak, fruity apple, agrestic (agrumex).

MS (EI, m/z) 196 (6, M$^+$); 178 (8); 139 (28); 126 (9); 111 (100); 96 (17); 85 (44); 69 (89); 57 (64); 41 (49).

8.3: 6-methyl-4-(2,2,3-trimethylcyclopentyl)hept-1-en-4-ol

Odour description: fruity, green, slightly agrestic; +4 h: fruity, green (hexenyl ester); +24 h: weak, fruity, slightly woody, rooty.

MS (EI, m/z) 220 (2); 197 (14); 179 (9); 139 (20); 127 (13); 111 (63); 95 (18); 85 (100); 69 (40); 57 (63); 55 (46); 41 (49).

8.4: 2-methyl-1-(2,2,3-trimethylcyclopentyl)prop-2-en-1-ol

Odour description: fruity, agrestic, floral; +4 h: fruity, slightly agrestic, piney, floral; +24 h: fruity, slightly agrestic, spicy, floral.

MS (EI, m/z) 182 (1, M+); 164 (5); 139 (5); 123 (2); 111 (50); 95 (24); 83 (8); 69 (100); 55 (47); 41 (38); 29 (6).

8.5: (+)-(1RS,1'S,3' RS)-1-(2',2',3'-Trimethylcyclopentyl)ethanol (ca. 20% ee)

Odour description: Piney, fruity, agrestic (borneol), woody, patchouli (but not so earthy), a bit spicy, resinous (sprouce).

IR (neat): ν=3357 (br. s, νO—H), 1468/1455 (m, δ$_{as}$CH$_3$), 1372/1366 (s, δ$_s$CH$_3$), 1145/1126/1024 (s, νC—O).

$^1$H NMR (CDCl$_3$): δ=0.64-1.25 (several s and d, 12H, 1-Me, 2'-Me$_2$, 3'-Me), 1.05-1.25 (m$_c$, 1H, 4'-H), 1.41-1.86 (m$_c$, 5H, 1'-H, 3'-H, 4'-H, 5'-H$_2$), 3.64-3.97 (4 m$_c$, 1H, 1-H).

$^{13}$C NMR (CDCl$_3$): δ=13.2-16.5 (several q, 2Me), 23.1/23.2/25.0/27.5 (4t, C-4'), 23.6-27.8 (several q, 2Me), 27.8/29.6/31.5/31.6 (4t, C-5'), 41.6/41.8/41.9/42.4 (4s, C-2'), 44.8/44.8/45.7/45.7 (4d, C-4'), 55.0/55.8/57.4/57.8 (4d, C-1'), 68.2/68.7/70.0/70.5 (4d, C-1).

MS (EI): m/z (%)=41 (50) [$C_3H_5^+$], 45 (42) [$C_2H_4OH^+$], 55 (62) [$C_4H_7^+$], 69 (100) [$C_5H_9^+$], 81 (22) [$C_6H_9^+$], 91 (6) [$C_7H_7^+$], 95 (38) [$C_7H_{11}^+$], 112 (21) [$C_8H_{16}^+$], 123 (27) [$M^+-CH_3-H_2O$], 138 (11) [$M^+-H_2O$], 141 (1) [$M^+-CH_3$], 156 (1) [Mt].

Polarimetry (c 1.02 in EtOH): $[\alpha]_D^{23}=+0.4°$, $[\alpha]_{578}^{23}=+0.4°$, $[\alpha]_{546}^{23}=+0.5°$, $[\alpha]_{436}^{23}=+1.0°$, $[\alpha]_{365}^{23}=+1.5°$.

8.6: 1-(2,2,3-trimethylcyclopent-3-enyl)propan-1-ol

Odour description: Very natural, agrestic, patchouli, a bit earthy/mossy, fruity (fenchyl acetate-type), slightly green.

$^1$H NMR (400 MHz, CDCl$_3$) δ5.26 (broad s, 1H); 3.66 (dt, 8.1, 4.6 Hz, 1H); 2.24 (m, 2H); 1.87 (td, 8.2, 4.8 Hz, 1H); 1.58

(m, 3H); 1.6-1.4 (m, 2H); 1.42 (broad s, 1H); 1.01 (s, 3H); 0.96 (t, 7.3 Hz, 3H); 0.95 (s, 3H).

$^{13}$C NMR (100 MHz, CDCl$_3$) δ148.2 (C$^{IV}$); 121.8 (CH); 73.4 (CH); 54.3 (CH); 46.7 (C$^{IV}$); 30.4 (CH$_2$); 29.6 (CH$_2$); 27.0 (CH$_3$); 20.5 (CH$_3$); 12.4 (CH$_3$); 10.3 (CH$_3$).

MS (EI, m/z) 168 (2, M$^+$); 150 (16); 135 (18); 121 (100); 107 (18); 95 (88); 79 (14); 67 (20); 59 (16); 55 (16); 41 (23).

EXAMPLE 9

1-((3S)-1,2,2-trimethylbicyclo[3.1.0]hex-3-yl)ethanol; ca. 20% ee

A drop of acetyl bromide (1 drop) was added to a mixture of activated (with 1N HCl) zinc (19.6 g, 0.3 mol), cuprous bromide (1.5 g, 0.01 mol) and 1-((1S)-2,2,3-trimethylcyclopent-3-enyl)ethanol (ca. 20% ee, 15.4 g, 0.3 mol) in diethyl ether (50 ml). After 10 minutes stirring, dibromomethane (52.0 g, 0.3 mol) was added and stirring at reflux continued for 6 h. The solid was filtered off and washed with MTBE. The combined organic phases were washed with water and diluted citric acid solution, dried (MgSO$_4$), concentrated in vacuo and distilled using a 5 cm Widmer-column to give 1-((3S)-1,2,2-trimethylbicyclo[3.1.0]hex-3-yl)ethanol (2.1 g, 12.5% yield, colourless liquid; GC/MS: 3 main diastereomeric pairs of enantiomers 33+30.5+20%). Analytical samples of the three main pairs of enantiomers were obtained by flash chromatography (MTBE/hexane 1:3)

Odour description: agrestic, minty, camphoraceous, woody, slightly patchouli.

Major diastereoisomer (first eluted): $^1$H NMR: δ3.67 (dq, J=9.6, 6.1, 1H), 1.57 (dd, J=12.0, 7.1, 1H), 1.37 (dt, J=11.7, 4.2, 1H), 1.30 (sb, 1H), 1.21-1.15 (m, 1H), 1.11 (d, J=6.1, 3H), 1.10 (s, 3H), 1.02 (s, 3H), 0.99-0.94 (m, 1H), 0.97 (s, 3H), 0.42 (t, J=4.1, 1H), 0.03 (dd, J=7.8, 4.7, 1H). $^{13}$C NMR: δ70.0 (d), 52.0 (d), 41.5 (s), 32.1 (s), 30.6 (t), 25.0 (q), 24.0 (q), 22.4 (d), 19.8 (q), 17.1 (q), 14.1 (t). MS: 153(1), 150(7), 135(56), 122(17), 121(100), 109(67), 107(71), 95(28), 93(29), 91(25), 83(33), 81(52), 79(23), 67(43), 55(43), 45(40), 43(50), 41(43).

Second major diastereoisomer (second eluted): $^1$H NMR: δ3.71 (dq, J=6.5, 6.3, 1H), 1.84-1.70 (m, 2H), 1.32 (sb, 1H), 1.20 (d, J=6.3, 3H), 1.15 (m, 1H), 1.05-1.00 (m, 1H), 1.02 (s, 3H), 0.97 (s, 3H), 0.87 (s, 3H), 0.74 (t, J=4.2, 1H), 0.11 (dd, J=7.9, 4.8, 1H). $^{13}$C NMR: δ68.7 (d), 51.7 (d), 41.0 (s), 32.0 (s), 28.6 (t), 23.8 (2q), 22.1 (d), 20.0 (q), 17.1 (q), 14.2 (t). MS: 168 (M$^+$, 0.1), 153(15), 150(7), 135(43), 123(15), 121 (100), 109(81), 107(49), 95(31), 93(27), 91(23), 85(27), 83(53), 81(61), 79(22), 68(32), 67(47), 55(46), 45(46), 43(67), 41(46).

Third major diastereoisomer (third eluted): $^1$H NMR: δ3.81 (m, 1H), 2.12-2.02 (m, 1H), 1.76-1.67 (m, 2H), 1.27 (sb, 1H), 1.11 (d, J=6.3, 3H), 1.05 (s, 3H), 1.05-0.98 (m, 1H), 1.01 (s, 6H), 0.74 (t, J=4.0, 1H), 0.11 (ddd, J=8.1, 4.3, 1.3, 1H). $^{13}$C NMR: δ67.2 (d), 57.1 (d), 44.3 (s), 33.2 (s), 31.3 (q), 27.2 (t), 25.4 (q), 24.4 (d), 20.8 (q), 18.2 (q), 17.4 (t). MS: 153(6), 150(5), 135(36), 122(12), 121(100), 109(33), 107 (39), 95(14), 93(19), 91(15), 83(24), 81(30), 67(26), 55(27), 45(25), 43(38), 41(28).

EXAMPLE 10

Fougère Aromatic Green-Fruity Composition for a Shower Gel

| Ingredient | parts by weight |
| --- | --- |
| Allyl amyl glycolate | 6 |
| Ambrofix (dodecahydro-3a,6,6,9a-tetramethyl-naphtho-(2,1-b)-furan) | 2 |
| Amyl salicylate | 60 |
| Carvone laevo ((R)-2-methyl-5-(prop-1-en-2-yl)cyclohex-2-enone) | 10 |
| Cedrylacetate | 40 |
| Citronellol | 60 |
| Coumarin | 30 |
| Dihydro eugenol | 6 |
| Dihydro myrcenol (2,6-dimethyloct-7-en-2-ol) | 60 |
| Ethyl vanillin at 10% in dipropyleneglycol (DPG) | 2 |
| Fenchyl acetate | 30 |
| Galaxolide ® 50 (1,3,4,6,7,8-hexahydro-4,6,6,7,8,8-hexamethyl-cyclopenta-amma-2-benzopyran) at 50% in isopropylmyristate (IPM) | 100 |
| Heliotropine | 10 |
| Hexenol-3-cis | 6 |
| Hexyl acetate | 12 |
| Hexyl cinnamic aldehyde | 100 |
| Ionone beta | 40 |
| Iso E super (1-(2,3,8,8-tetramethyl-1,2,3,4,5,6,7,8-octahydronaphthalen-2-yl)-ethanone) | 60 |
| Labienoxime (2,4,4,7-tetramethyl-6,8-nonadiene-3-one-oxime) at 1% in IPM-TEC (isopropylmyristate-triethylcitrate mixture 90/10) | 2 |
| Linalool | 160 |
| Maltol isobutyrate at 10% in DPG | 4 |
| Radjanol (2-ethyl-4-(2,2,3-trimethylcyclopent-3-enyl)but-2-en-1-ol) | 16 |
| Stemone ® (5-methyl-3-heptanone oxime) | 4 |
| Terpinyl acetate (2-(4-methylcyclohex-3-enyl)propan-2-yl acetate) | 80 |
| 1-(2,2,3-Trimethylcyclopent-3-en-1-yl)ethanol (compound 4.9) | 100 |
| Total: | 1000 |

This fougère fragrance with a spearmint leaf effect and fruity green undertones in the direction of apple, provides a green-aromatic freshness to shower gel formulations, which is greatly enhanced by the patchouli character of 1-(2,2,3-trimethylcyclopent-3-en-1-yl)ethanol. Incorporation of this new odorant conveys a natural resinous-woody, balsamic character that enhances the fresh-aromatic theme of the composition without dominating the fragrance with its patchouli note. 1-(2,2,3-trimethylcyclopent-3-en-1-yl)ethanol also stresses the fresh eucalyptus and spearmint effect, but most importantly renders it the construction of a fougère theme possible without incorporation of oak moss. Without the woody-camphoraceous-earthy patchouli scent of 1-(2,2,3- trimethylcyclopent-3-en-1-yl)ethanol with its slightly spicy accents and fruity-green facets that idea.

EXAMPLE 11

Fougère Aromatic Lavender Composition for a Masculine Eau-De-Cologne

| Ingredient | parts by weight |
|---|---|
| Agrumex (2-tert-butylcyclohexyl acetate) | 80 |
| Allyl amyl glycolate | 6 |
| Ambrofix (dodecahydro-3a,6,6,9a-tetramethyl-naphtho-(2,1-b)-furan) | 20 |
| Anise oil | 2 |
| Bourgeonal T (3-(4-tert-butylphenyl)propanal) | 6 |
| Clove bud oil | 2 |
| Cyclohexal | 80 |
| Damascenone (1-(2,6,6-trimethylcyclohexa-1,3-dienyl)but-2-en-1-one) at 10% in dipropyleneglycol (DPG) | 4 |
| Dimethyl phenyl ethyl carbinol (2-methyl-4-phenyl-2-butanol) | 20 |
| Fennaldehyde (3-(4-methoxyphenyl)-2-methylpropanal) | 10 |
| Fixolide (1-(3,5,5,6,8,8-hexamethyl-5,6,7,8-tetrahydronaphthalen-2-yl)-ethanone) | 120 |
| Floralozone (3-(4-ethylphenyl)-2,2-dimethylpropanal) | 2 |
| Hedione ® HC (methyl 2-(3-oxo-2-pentylcyclopentyl)acetate) | 160 |
| Hexenol-3-cis | 4 |
| Irone alpha (4-(2,5,6,6-tetramethylcyclohex-2-enyl)but-3-en-2-one) | 2 |
| Iso E super (1-(2,3,8,8-tetramethyl-1,2,3,4,5,6,7,8-octahydronaphthalen-2-yl)-ethanone) | 120 |
| Lavender oil | 80 |
| Lemon oil | 40 |
| Liffarome ((Z)-hex-3-enyl methyl carbonate) | 2 |
| Ligustral (2,4-dimethylcyclohex-3-enecarbaldehyde) | 2 |
| Mandarin oil | 14 |
| Methyl cedryl ketone | 80 |
| Radjanol (2-ethyl-4-(2,2,3-trimethylcyclopent-3-enyl)but-2-en-1-ol) | 20 |
| Spearmint oil | 2 |
| Tropional (3-(benzo[d][1,3]dioxol-5-yl)-2-methylpropanal) | 30 |
| Vanillin | 2 |
| 1-(2,2,3-trimethylcyclopent-3-enyl)prop-2-en-1-ol | 90 |
| Total: | 1000 |

This composition presents a fresh cologne character with a particular emphasis on a true natural lavender effect. The lavender is blended with a rich woody ambery and powdery background, while the heart is a soft floral with watery connotations. 1-(2,2,3-trimethylcyclopent-3-enyl)prop-2-en-1-ol (Ex. 4.12) brings an agrestic patchouli character to the composition. It enhances also the crisp and natural feeling while improving the lift and freshness.

The invention claimed is:

1. A compound of formula (I) which has a flavor or fragrance

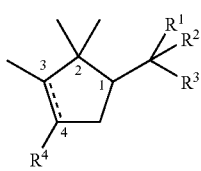

(I)

wherein
$R^4$ is hydrogen and the bond between C-3 and C-4 is a single bond or the dotted line together with the bond between C-3 and C-4 represents a double bond; or
$R^4$ is methylene, forming with C-3 and C-4 a cyclopropane ring;
$R^3$ is hydrogen, $C_1$, $C_2$, $C_3$, $C_4$, $C_5$, $C_6$ alkyl, or $C_2$, $C_3$, $C_4$, $C_5$, $C_6$ alkenyl; and
I) $R^1$ and $R^2$ together with the carbon atom to which they are attached form a carbonyl group; or
II) $R^1$ is hydroxyl and $R^2$ is selected from $C_1$, $C_2$, $C_3$ alkyl, and $C_2$, $C_3$, $C_4$ alkenyl.

2. A compound according to claim 1 wherein $R^4$ of the compound of formula (I) is hydrogen and the dotted line together with the bond between C-3 and C-4 represents a double bond.

3. A compound according to claim 1 wherein the compound of formula (I) is selected from the group consisting of:
1-(2,2,3-trimethylcyclopent-3-enyl)propan-1-ol;
1-(2,2,3-trimethylcyclopent-3-enyl)propan-1-one;
2-(2,2,3-trimethylcyclopent-3-enyl)butan-2-ol;
2-methyl-1-(2,2,3-trimethyl-cyclopent-3-enyl)butan-1-ol;
3-methyl-1-(2,2,3-trimethylcyclopent-3-enyl)butan-1-ol;
1-(2,2,3-trimethylcyclopent-3-enyl)pent-4-en-1-ol;
1-(2,2,3-trimethylcyclopent-3-enyl)hex-5-en-1-ol;
2,2-dimethyl-1-(2,2,3-trimethylcyclopent-3-enyl)but-3-en-1-ol;
(E)-1-(2,2,3-trimethylcyclopent-3-enyl)but-2-en-1-ol;
(Z)-1-(2,2,3-trimethylcyclopent-3-enyl)but-2-en-1-ol;
1-(2,2,3-trimethylcyclopent-3-enyl)but-3-en-1-ol;
1-(2,2,3-trimethylcyclopent-3-enyl)ethanol;
2-methyl-1-(2,2,3-trimethylcyclopent-3-enyl)prop-2-en-1-ol;
1-(2,2,3-trimethylcyclopent-3-enyl)prop-2-en-1-ol;
2-methyl-1-(2,2,3-trimethylcyclopent-3-enyl)butan-1-one;
3-methyl-1-(2,2,3-trimethylcyclopent-3-enyl)butan-1-one;
1-(2,2,3-trimethylcyclopent-3-enyl)pent-4-en-1-one;
1-(2,2,3-trimethylcyclopent-3-enyl)hept-6-en-1-one;
2,2-dimethyl-1-(2,2,3-trimethylcyclopent-3-enyl)but-3-en-1-one;
(E)-1-(2,2,3-trimethylcyclopent-3-enyl)but-2-en-1-one;
(Z)-1-(2,2,3-trimethylcyclopent-3-enyl)but-2-en-1-one;
1-(2,2,3-trimethylcyclopent-3-enyl)but-3-en-1-one;
1-(2,2,3-trimethylcyclopent-3-enyl)ethanone;
3-(2,2,3-trimethylcyclopent-3-enyl)hex-5-en-3-ol;
2-(2,2,3-trimethylcyclopent-3-enyl)pentan-2-ol;
6-methyl-4-(2,2,3-trimethylcyclopent-3-enyl)hept-1-en-4-ol;
2-(2,2,3-trimethylcyclopent-3-enyl)hex-5-en-2-ol;
4-(2,2,3-trimethylcyclopent-3-enyl)oct-7-en-4-ol;
2-(2,2,3-trimethylcyclopent-3-enyl)oct-7-en-2-ol;
3,3-dimethyl-2-(2,2,3-trimethylcyclopent-3-enyl)pent-4-en-2-ol;
3,3-dimethyl-4-(2,2,3-trimethylcyclopent-3-enyl)hepta-1,6-dien-4-ol;
2-(2,2,3-trimethylcyclopent-3-enyl)propan-2-ol; 2,2,3-trimethylcyclopentanecarbaldehyde;
3-methyl-1-(2,2,3-trimethylcyclopentyl)butan-1-ol;
3-methyl-1-(2,2,3-trimethylcyclopentyl)butan-1-one;
6-methyl-4-(2,2,3-trimethylcyclopentyl)hept-1-en-4-ol;
2-methyl-1-(2,2,3-trimethylcyclopentyl)prop-2-en-1-ol;
(+)-(1RS,1'S,3'RS)-1-(2',2',3'-trimethylcyclopentyl);
1-(2,2,3-trimethylcyclopent-3-enyl)propan-1-ol; and
1-(1,2,2-trimethylbicyclo[3.1.0]hex-3-yl)ethanol.

4. A method of improving, enhancing or modifying a fragrance application the method comprising the step of:
adding thereto of an olfactory acceptable amount of a compound of formula (I) as defined in claim 1, or a mixture thereof.

5. A fragrance application comprising as fragrance a compound of formula (I) as defined in claim 1, or a mixture thereof; and a consumer product base.

6. A fragrance application according to claim 4 wherein the consumer product base is selected from the group consisting of: fine fragrances, household products, laundry products, body care products, cosmetic and air-care products.

7. A compound of formula (I)

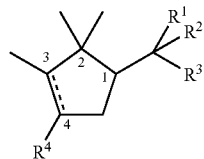
(I)

wherein $R^4$ is hydrogen and the bond between C-3 and C-4 is a single bond or the dotted line together with the bond between C-3 and C-4 represents a double bond; or $R^4$ is methylene, forming with C-3 and C-4 a cyclopropane ring;

$R^3$ is hydrogen, $C_1$, $C_2$, $C_3$, $C_4$, $C_5$, $C_6$ alkyl, or $C_2$, $C_3$, $C_4$, $C_5$, $C_6$ alkenyl; and I) $R^1$ and $R^2$ together with the carbon atom to which they are attached form a carbonyl group; or II) $R^1$ is hydroxyl and $R^2$ is selected from $C_1$, $C_2$, $C_3$ alkyl, and $C_2$, $C_3$, $C_4$ alkenyl;

with the proviso that 2,2,3-trimethyl-cyclopent-3-enecarbaldehyde, 2,2,3-trimethylcyclopentanecarbaldehyde, and 1-(2,2,3-trimethylcyclopent-3-enyl)ethanol are excluded.

* * * * *